US008424738B2

(12) United States Patent
Kasvikis

(10) Patent No.: US 8,424,738 B2
(45) Date of Patent: Apr. 23, 2013

(54) ATTACHABLE CLAMP FOR SURGICAL STAPLER

(75) Inventor: Dino Kasvikis, Middletown, CT (US)

(73) Assignee: Covidien LP, Mansfield, MA (US)

( * ) Notice: Subject to any disclaimer, the term of this patent is extended or adjusted under 35 U.S.C. 154(b) by 176 days.

(21) Appl. No.: 12/467,327

(22) Filed: May 18, 2009

(65) Prior Publication Data

US 2009/0302093 A1    Dec. 10, 2009

Related U.S. Application Data

(60) Provisional application No. 61/058,672, filed on Jun. 4, 2008.

(51) Int. Cl.
*A61B 17/072*    (2006.01)

(52) U.S. Cl.
USPC .......................................... 227/176.1; 227/19

(58) Field of Classification Search .... 227/175.1–182.1, 227/19; 81/339, 340; 606/219–220; 74/575, 74/578
See application file for complete search history.

(56) References Cited

U.S. PATENT DOCUMENTS

| 3,080,564 | A | * | 3/1963 | Strekopitov et al. | .......... 227/153 |
| 3,269,630 | A | | 8/1966 | Fleischer | |
| 3,315,863 | A | | 4/1967 | O'Dea | |
| 3,589,589 | A | * | 6/1971 | Akopov | ......................... 227/153 |
| 3,692,224 | A | * | 9/1972 | Astafiev et al. | ................. 227/19 |
| 4,216,891 | A | | 8/1980 | Behlke | |
| 4,344,420 | A | * | 8/1982 | Forder | .......................... 600/232 |
| 4,354,628 | A | | 10/1982 | Green | |
| 4,383,634 | A | * | 5/1983 | Green | .............................. 227/19 |
| 4,506,671 | A | | 3/1985 | Green | |
| 4,530,453 | A | | 7/1985 | Green | |
| 4,566,620 | A | | 1/1986 | Green | |
| 4,568,009 | A | | 2/1986 | Green | |
| 4,589,582 | A | | 5/1986 | Bilotti | |
| 4,617,928 | A | | 10/1986 | Alfranca | |
| 4,665,916 | A | | 5/1987 | Green | |

(Continued)

FOREIGN PATENT DOCUMENTS

EP    0 246 870 A2    11/1987
EP    1 550 412 A2    7/2005

(Continued)

OTHER PUBLICATIONS

European Search Report for corresponding EP 10 25 0934, date of completion is Aug. 19, 2010 (3 pages).

(Continued)

*Primary Examiner* — Rinaldi Rada
*Assistant Examiner* — Andrew M Tecco

(57) ABSTRACT

A surgical fastener applying instrument including a handle portion, an elongated portion, a pair of jaw members and a removable clamp. One of the jaw members contains a plurality of fasteners arranged in at least one row substantially transverse to a longitudinal axis of the elongated portion. At least one of the jaw members is movable with respect to the other between an open position and an approximated position for engaging body tissue therebetween. The removable clamp has an elongated member and a tissue clamping surface extending substantially transverse to a longitudinal axis of the elongated member. The clamp is movable from a proximal position to a distal position for engaging body tissue and is releasably mountable to the elongated portion of the instrument.

11 Claims, 6 Drawing Sheets

U.S. PATENT DOCUMENTS

| | | | |
|---|---|---|---|
| 4,684,051 A | | 8/1987 | Akopov et al. |
| 4,715,520 A | * | 12/1987 | Roehr et al. .................... 227/19 |
| 4,788,978 A | | 12/1988 | Strekopytov et al. |
| 4,802,614 A | * | 2/1989 | Green et al. .................... 227/19 |
| 4,819,853 A | | 4/1989 | Green |
| 4,834,112 A | * | 5/1989 | Machek et al. ............... 600/587 |
| 4,869,414 A | | 9/1989 | Green et al. |
| 4,881,545 A | | 11/1989 | Isaacs et al. |
| 4,915,100 A | | 4/1990 | Green |
| 5,100,042 A | * | 3/1992 | Gravener et al. .......... 227/176.1 |
| 5,242,457 A | | 9/1993 | Akopov et al. |
| 5,344,060 A | * | 9/1994 | Gravener et al. .......... 227/180.1 |
| 5,405,073 A | | 4/1995 | Porter |
| 5,452,836 A | | 9/1995 | Huitema et al. |
| 5,465,894 A | | 11/1995 | Clark et al. |
| 5,509,596 A | * | 4/1996 | Green et al. ............... 227/176.1 |
| 5,547,117 A | | 8/1996 | Hamblin et al. |
| 5,558,266 A | * | 9/1996 | Green et al. ............... 227/178.1 |
| 5,579,978 A | * | 12/1996 | Green et al. ............... 227/175.3 |
| 5,607,094 A | | 3/1997 | Clark et al. |
| 5,653,373 A | | 8/1997 | Green et al. |
| 5,662,260 A | | 9/1997 | Yoon |
| 5,676,674 A | | 10/1997 | Bolanos et al. |
| 5,706,997 A | * | 1/1998 | Green et al. ............... 227/175.2 |
| 5,706,998 A | * | 1/1998 | Plyley et al. ............... 227/175.3 |
| 5,810,240 A | * | 9/1998 | Robertson .................. 227/175.2 |
| 5,928,264 A | | 7/1999 | Sugarbaker et al. |
| 6,053,908 A | * | 4/2000 | Crainich et al. .................. 606/1 |
| 6,805,273 B2 | | 10/2004 | Bilotti et al. |
| 6,988,650 B2 | | 1/2006 | Schwemberger et al. |
| 7,147,139 B2 | | 12/2006 | Schwemberger et al. |
| 7,204,404 B2 | | 4/2007 | Nguyen et al. |
| 7,207,472 B2 | | 4/2007 | Wukusick et al. |
| 7,278,563 B1 | | 10/2007 | Green |
| 7,401,721 B2 | | 7/2008 | Holsten et al. |
| 7,472,814 B2 | | 1/2009 | Mastri et al. |
| 2002/0065523 A1 | | 5/2002 | McAlister |
| 2005/0139636 A1 | | 6/2005 | Schwemberger et al. |
| 2005/0145672 A1 | | 7/2005 | Schwemberger et al. |
| 2005/0247753 A1 | | 11/2005 | Kelly et al. |
| 2005/0263563 A1 | * | 12/2005 | Racenet et al. ............ 227/176.1 |
| 2006/0163312 A1 | * | 7/2006 | Viola et al. ................ 227/175.1 |
| 2007/0039996 A1 | * | 2/2007 | Mather et al. .............. 227/176.1 |
| 2007/0039997 A1 | * | 2/2007 | Mather et al. .............. 227/176.1 |
| 2007/0095877 A1 | * | 5/2007 | Racenet et al. ............ 227/175.2 |
| 2007/0187456 A1 | | 8/2007 | Viola et al. |
| 2008/0078800 A1 | | 4/2008 | Hess et al. |

FOREIGN PATENT DOCUMENTS

| | | |
|---|---|---|
| EP | 1 875 868 A1 | 1/2008 |
| EP | 1 935 354 A2 | 6/2008 |
| EP | 1 550 411 B1 | 7/2009 |
| EP | 2130501 | 12/2009 |
| GB | 2029754 | 3/1980 |
| WO | WO 02/30296 | 4/2002 |
| WO | WO 2006/055385 | 5/2006 |

OTHER PUBLICATIONS

European Search Report EP 09251240 dated Oct. 5, 2009. (8 pages).
European Search Report for Application No. 09251420.7 dated Sep. 7, 2009. (2 pages).

* cited by examiner

ATTACHABLE CLAMP FOR SURGICAL STAPLER

This application claims priority to provisional application Ser. No. 61/058,672, filed Jun. 4, 2008, the entire contents of which are incorporated herein by reference.

BACKGROUND

1. Technical Field

The present disclosure relates generally to a surgical instrument and, more specifically, to a surgical instrument for clamping tissue, approximating anvil and cartridge assemblies, and for surgically joining tissue.

2. Background of Related Art

Surgical stapling instruments used for applying parallel rows of staples through compressed living tissue are well known in the art, and are commonly used, for example, for closure of tissue or organs prior to transection, prior to resection, in anastomoses, and for occlusion of organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

In use, a surgeon approximates the anvil and cartridge members and then fires the instrument to emplace staples in tissue. Additionally, the surgeon may use the same instrument or a separate instrument to cut the tissue adjacent, across or between the row(s) of staples.

SUMMARY

The present disclosure relates in one aspect to a surgical fastener applying instrument including a handle portion, an elongated portion, and a pair of jaw members disposed adjacent a distal end of the elongated portion. At least one of the jaw members is movable with respect to the other jaw member between an open position and an approximated position for engaging body tissue therebetween. One of the jaw members contains a plurality of fasteners arranged in at least one row substantially transverse to a longitudinal axis of the elongated portion. A removable clamp having an elongated member and a tissue clamping surface extending substantially transverse to a longitudinal axis of the elongated member is releasably mounted to the elongated portion of the instrument.

In a preferred embodiment, a tissue-contacting surface of each of the jaw members is disposed substantially transverse to a longitudinal axis of the elongated portion. A knife can be provided for movement between a proximal and distal position to cut tissue.

An embodiment of the present disclosure includes jaw member(s) (e.g., a cartridge assembly and/or an anvil assembly) that are configured to be removable. The cartridge assembly can include two (or more) rows of staples with a knife disposed between them. In another embodiment, the cartridge assembly includes one row of staples, and includes a knife disposed adjacent the row of staples. In another embodiment, the knife is on one side of two or more rows of staples.

A hook can be provided to secure the clamp on either side of the instrument. The hook can be detachable. In one embodiment, a ratchet allows the clamp to move in one direction and restricts movement in an opposite direction. In another embodiment, a locking pin and opening allows the clamp to move in one direction and restricts movement in an opposite direction.

The present disclosure also relates in another aspect to a clamp configured for attachment to a surgical stapling instrument having a plurality of staples arranged in at least one row substantially transverse to a longitudinal axis of the instrument. The clamp has an elongated body portion and a clamping head. The elongated body portion is configured for removable attachment to an elongated body of the surgical fastening instrument for movement between a proximal and distal position along the instrument. The clamp may further include a ratchet engageable with the elongated portion of the instrument.

The present disclosure also relates to a method of performing a lower anterior resection. The method includes the step of providing a surgical fastening instrument including a handle portion, an elongated portion, a pair of jaw members and a clamp. The elongated portion extends distally from the handle portion. The pair of jaw members is disposed adjacent a distal end of the elongated portion and one of the jaw members contains a plurality of fasteners positioned therein arranged in a row substantially transverse to a longitudinal axis of the elongated portion. The clamp is removably attached to the elongated portion of the instrument. The clamp is preferably independently movable with respect to the jaw members. The method also includes the steps of moving the clamp from a proximal position towards a distal position to engage intestinal tissue, cleaning the interior of the intestinal tissue, moving at least one of the jaw members with respect to the other from an open position towards an approximated position to engage intestinal tissue adjacent the intestinal tissue engaged by the clamp, and joining the intestinal tissue between the jaw members by applying a plurality of fasteners to the tissue in a direction substantially parallel to the longitudinal axis of the elongated portion.

An embodiment of the disclosed method includes the step of cutting intestinal tissue adjacent the joined intestinal tissue.

BRIEF DESCRIPTION OF FIGURES

Various embodiments of the presently disclosed surgical stapling instrument are disclosed herein with reference to the drawings, wherein.

DETAILED DESCRIPTION

Figure 1:
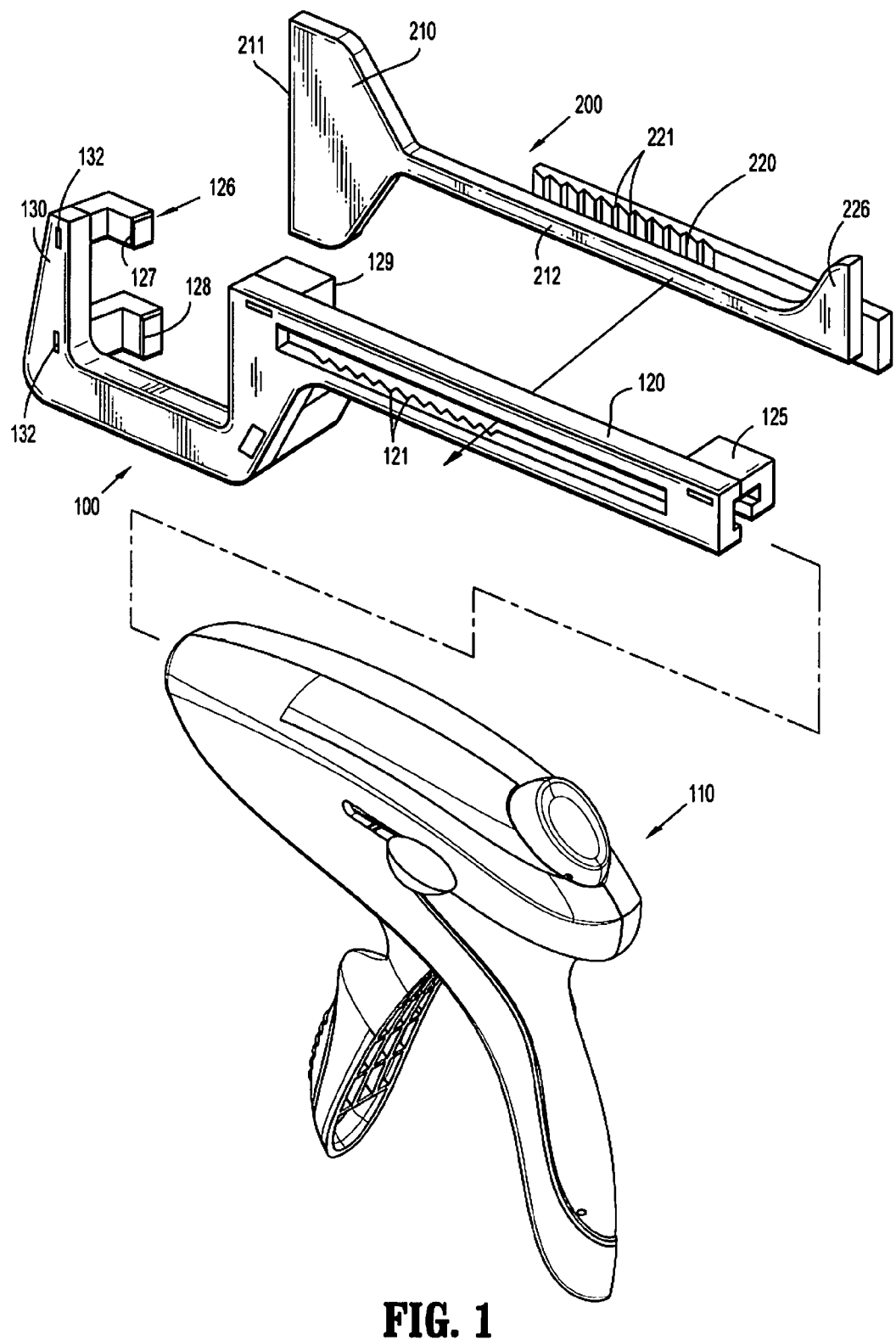
FIG. 1 is an exploded perspective view of a first embodiment of a portion of the surgical stapling instrument and the clamp of the present disclosure.

Embodiments of the presently disclosed surgical fastening instrument are described in detail with reference to the drawings, wherein like reference numerals designate corresponding elements in each of the several views. In the drawings and the description that follows, the term "proximal" refers to the end of the surgical stapling instrument that is closer to the operator, whereas the term "distal" refers to the end of the surgical stapling instrument that is further from the operator. It should be appreciated that the instrument described and illustrated herein is configured to fire fasteners in the form of surgical staples advanced against an anvil surface for formation thereof; however, it can also be used to fire other forms of staples, fasteners, clips, as well as two part fasteners, made of metallic or polymeric material.

Figure 7:
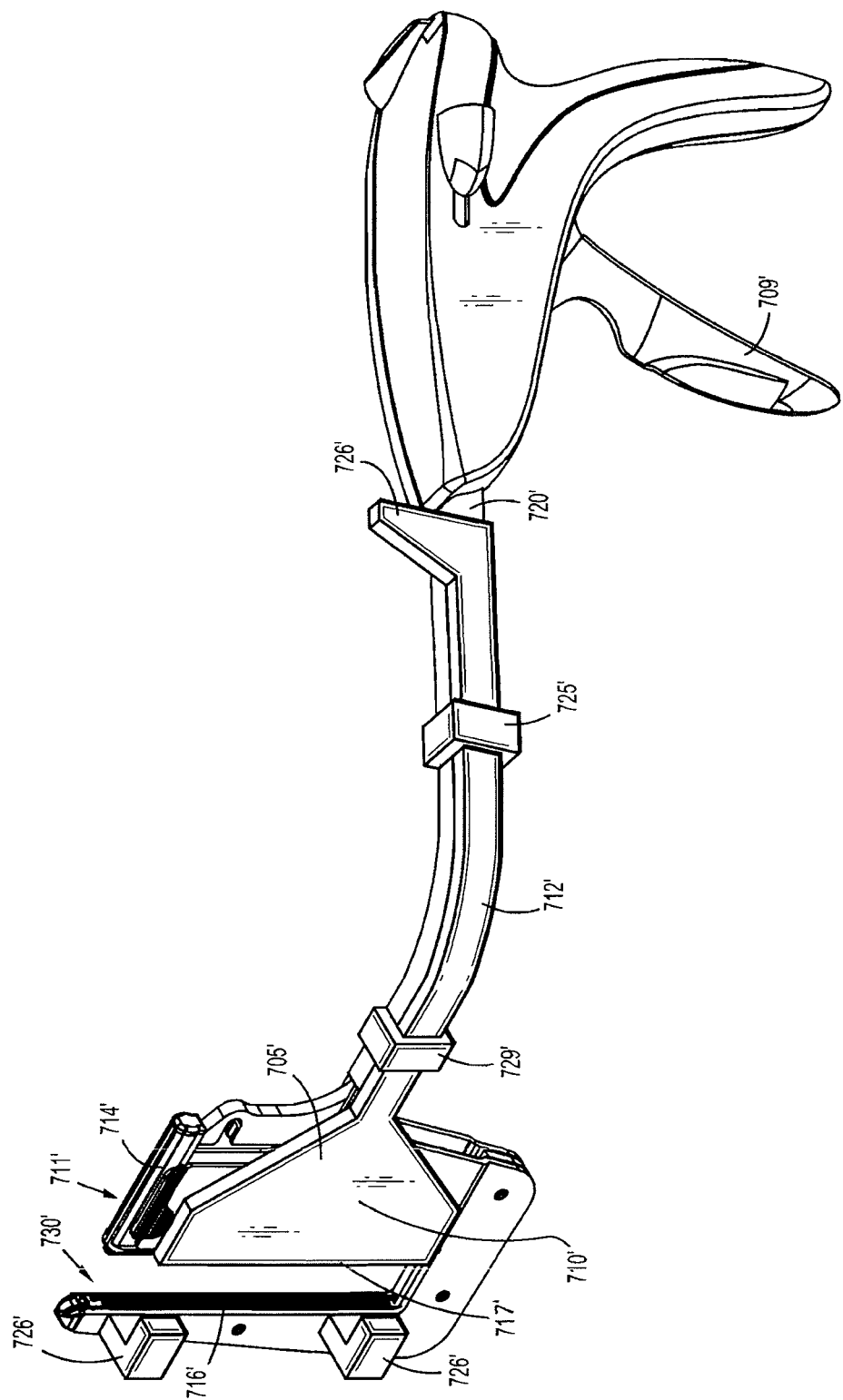
FIG. 7 is a perspective view of an alternate embodiment showing a stapling instrument and clamp with a curved shaft.

The surgical stapling instrument of a first embodiment of the present disclosure is illustrated in FIG. 1 and is indicated generally by reference numeral 100. The instrument has a substantially straight elongated portion 120 as shown. However, it alternately could be curved or angled as disclosed in commonly-owned U.S. Patent Application Serial No. 2007/0187456 filed on Apr. 10, 2007, the entire contents of which are hereby incorporated by reference herein. An example of a curved elongated portion is also shown in the embodiment of FIG. 7 discussed below.

Surgical stapling instrument 100 is configured for approximating its jaw members and emplacing staples or fasteners in tissue. It can also be configured to cut tissue. It is also configured to receive a slidable clamping member described in more detail below. Generally, surgical stapling instrument 100 includes a handle portion 110, elongated portion 120, and a pair of jaw members which includes a cartridge assembly and an anvil assembly. (The cartridge and anvil assembly are shown schematically in FIG. 1; more detail of these assemblies are shown on FIG. 6). The cartridge assembly is preferably removably mounted to the distal end of the instrument 100. The anvil assembly, either separate from or connected to the cartridge assembly, may also be removably mounted to the instrument.

Surgical stapling instrument 100 also includes a clamp 200. Clamp 200 includes an elongated portion or member 212 and an enlarged clamping head 210. The clamping head 210 can be integral with the elongated member 212 or alternatively can be a separate component attached to the member 212. Clamping head has a tissue contacting surface 211 extending substantially transverse to a longitudinal axis of the elongated portion 212 and the longitudinal axis of the elongated portion 120 of instrument 100. As shown, the clamping head 210 has a height greater than a height of the elongated member 212 and a height close to the length of the rows of fasteners. Clamp 200 is removably mountable to the instrument 100 as described in more detail below. Upon activation of clamp 200 (discussed in detail below), clamp head 210 is translated distally to compress tissue (e.g., an organ), thus temporarily occluding the organ, for instance, between the tissue contacting surface 211 at the distal end of clamp 200 and the instrument jaw member 130 housing the anvil assembly. Additionally, distal translation of clamp 200 allows the user to help ascertain where the staples will be emplaced.

After clamp head 210 has been advanced and the organ is occluded, the user approximates the jaw members about the organ. Subsequently, the staples may be fired (e.g., simultaneously or sequentially) from the staple cartridge and emplaced in the organ held between the jaw members. Further, the user may then transect or cut the stapled organ with a knife. In some embodiments, the cutting may be done substantially simultaneously with stapling of the organ by the provision of knife in the instrument which is advanced as the staples are fired. Alternatively, a knife could be provided in the instrument which has a separate mechanism for advancing the knife independent of the staple firing. The knife could be provided either adjacent at least one of the rows of staples, e.g. between the rows or alongside an outer row.

Figure 5:
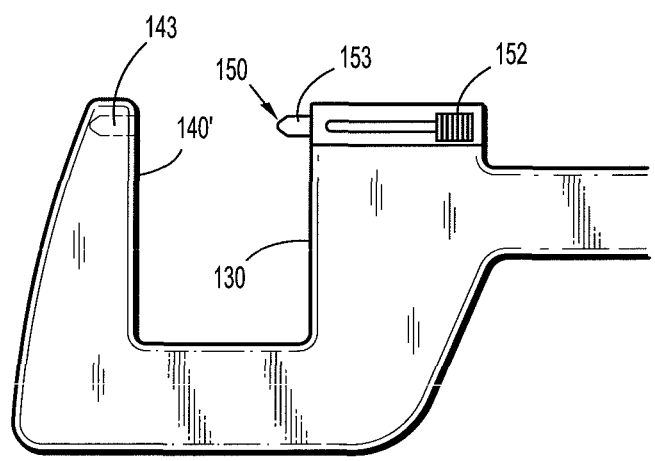
FIG. 5 is a side view of a tissue pin of the clamp of the present disclosure.

Additionally, the use of at least one tissue pin 150, such as shown in FIG. 5, may be used to help secure the tissue for clamping. Tissue pin 150 of clamp 200 can be manually advanced and retracted by slider 152. The distal portion 153 engages slot 143 of anvil frame 140' when the alignment pin is in the advanced position. This alignment pin can be used in addition to an alignment pin for the stapling cartridge.

Figure 1A:
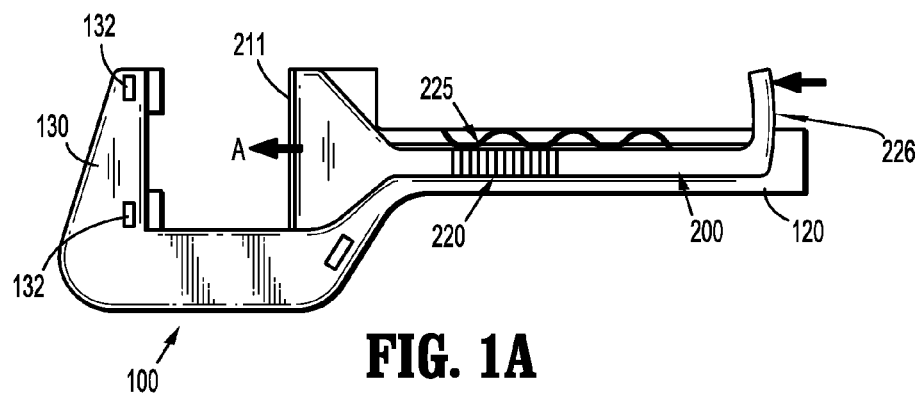
FIG. 1A is a side view of the instrument of FIG. 1 showing the clamp attached to the instrument and in the retracted position.

In its proximal position, clamp head 210 is preferably located adjacent the retracted (unapproximated) cartridge as shown for example in FIG. 1A (and FIG. 6), with clamping head 210 in this embodiment approximating (FIG. 1) or slightly less than (FIG. 6) the height of the staple line. It is envisioned that tissue-contacting surface 211 of clamp 200 could be smooth, jagged, serrated (e.g., to interlock with tissue), rounded, flat, angled, beveled, bent (to provide a greater surface area), etc., or any combination thereof. It is further envisioned that a portion of the anvil assembly (e.g., part of the anvil 316 of FIG. 6 or adjacent thereto) could include a groove (not shown) for accepting clamp head 210 to help secure tissue therebetween.

Figure 1B:
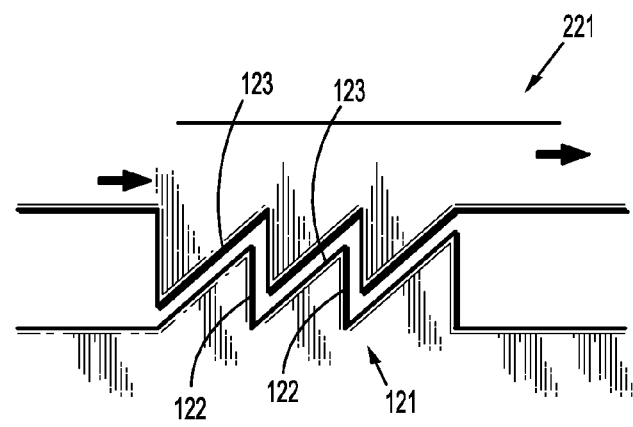
FIG. 1B is an enlarged view of a portion of the locking rack of FIG. 1.

Clamp assembly 200 is removably mounted to the instrument. In the embodiment of FIG. 1A, the elongated body portion 120 of instrument 100 has a plurality of teeth 121 which are engaged by the locking rack 220 of the clamp 200. The locking rack 220, having a series of teeth 221, extends along a portion of the elongated portion 212 of the clamp 200 and is configured for stepped advancement along the teeth 121 for controlled movement of the clamp 200 distally to an advanced position to clamp tissue between its distal end 211 and the proximal surface of the anvil receiving jaw portion 130. This ratchet mechanism is designed to allow movement in the distal direction, due to the angled wall 123 of the teeth 121, but prevent retraction during the advancement of the clamp due to the straight wall 122 of the teeth, shown in the enlarged view of FIG. 1B. Thus, the flats on the teeth 121 maintain the clamp in the desired longitudinal position, restricting the proximal force applied by the compressed tissue. The spring 225 is provided to bias the clamp 200 toward the instrument to ensure contact between the teeth of both components. An additional spring (not shown) could be provided to pull the sliding feature into the locked position.

As can be appreciated, the teeth 121 are positioned on the elongated portion 120 spaced from the approximation mechanism and the firing mechanism which are slidably received within the elongated body portion of the instrument and not shown in the drawings.

To advance the clamp 200, the handle 226 is pushed forward by the user in the direction of the arrow of FIG. 1A. To release the clamp 200 after the clamping function, the handle 226 is lifted upwardly, disengaging the teeth 221 of the clamp assembly 200 so they can bypass teeth 121 of the instrument.

A pair of retaining hooks 126 is provided on the distal portion of the instrument 100, extending radially and then proximally at regions 127, 128, respectively, to help retain the clamp to the instrument 100 and maintain alignment when advanced.

It is envisioned that the components can be configured to enable mounting of the clamp on either side of the instrument. In this embodiment, the hooks 126 of the instrument could optionally be configured to be removed and inserted on the other side of the instrument, through slots 132 of FIG. 1, if desired, to enable placement of the clamp 200 on the other side of the instrument 100. A series of teeth would be provided on the other side of the rack 220 (not shown) which would then engage a series of teeth (e.g. teeth 121) of instrument 100 in a similar manner. In this manner, the clamp 200 can be used on either side of the instrument. Again, these teeth would be positioned adjacent to and without interfering with the approximation and firing mechanisms contained within elongated portion 120 of the instrument.

Figure 6A:
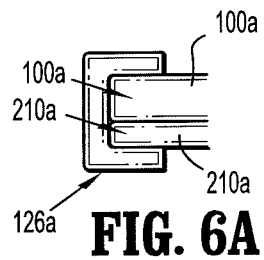
FIG. 6A is a top view of an alternate embodiment of the clamp securing hooks of the present disclosure.
Figure 6B:
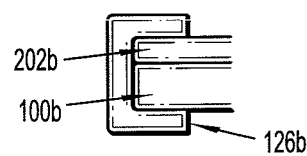
FIG. 6B is a top view of another alternate embodiment of the clamp securing hooks of the present disclosure.
Figure 6:
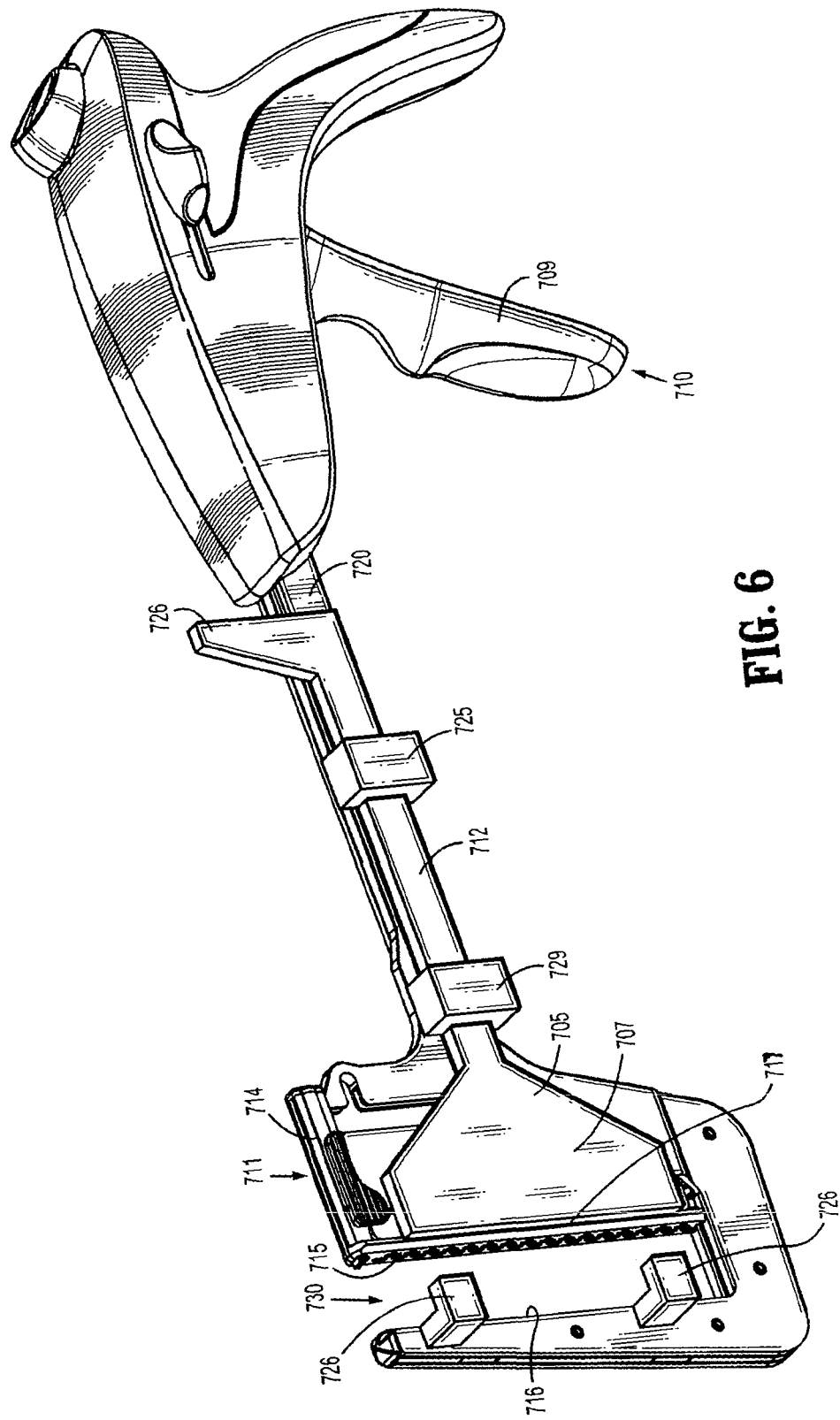
FIG. 6 is a perspective view of the clamp of the present disclosure attached to a stapling instrument with a straight shaft.

FIG. 6 illustrates the clamp 705 mounted on the other side of the instrument of that shown in FIG. 1, and also illustrates an entire stapling instrument similar to the instrument 100 of FIG. 1. Clamp 705 has an elongated member 712 and an enlarged clamping head 707 similar to clamp 200 with a tissue clamping surface 717. Instrument 700 has a handle portion 710, an elongated body portion 720, a cartridge 714 of a cartridge assembly 711 movable into approximation with an anvil 716 of anvil assembly 730. Retaining hooks 726 can be removably attachable to the anvil assembly 730 through slots (not shown) similar to slots 132 of FIG. 1 for mounting on either side. Hooks 725, 729 extending from body portion 702 are similar to hooks 125, 129 of FIG. 1 and are configured and dimensioned to secure clamp 705 to the instrument 700, while still enabling sliding of the clamp. Handle 726 advances the clamp 705. A ratchet mechanism allows for movement of the clamp in a distal direction. Squeezing of handle 709 approximates the cartridge 714, and subsequent squeezing advances a pusher mechanism to fire the staples through staple slots 715 aligned in linear rows substantially transverse to the longitudinal axis of elongated body portion 720. Such handle and approximation and firing mechanisms are disclosed in commonly assigned U.S. Pat. No. 7,407,076, the entire contents of which are incorporated herein by reference.

The stapling instrument 700' of FIG. 7 is the same as instrument 700 of FIG. 6 except for the curved elongated portion 720'. Similarly, clamp 705' is the same as clamp 705 of FIG. 6, except for the curved elongated member or body portion 712'. In all other respects the clamp and stapling instrument are the same as in FIG. 6 and therefore will not be described further herein as like parts have been provided with "prime" designations in FIG. 7.

Turning back to FIGS. 1 and 1A, proximal and distal hooks 125, 129, preferably similarly configured, extend radially from the elongated body 120 for securing the clamp 200 to the elongated body 120 of instrument 100. The hooks 125, 129 are configured to surround a portion of the elongated member 212 of clamp 200 to retain the elongated member 212. The hooks are dimensioned to prevent inadvertent detachment of the clamp 200, while allowing for longitudinal movement of the clamp 200 to advance and retract the clamp head 210.

In the alternate embodiment of FIG. 6A, instead of removable distal hooks 126 as in FIG. 1, the hooks are non-removably secured to the instrument. A pair of hooks 126a is positioned on both sides of the instrument to enable the clamp 210a to be placed on either side of instrument 100a. Only the top pair of hooks is shown in the top view of FIG. 6A as the bottom hooks are positioned underneath. The left and right top hook and the left and right bottom hook can each be integral and attached to the anvil portion of the instrument or integral with the instrument, e.g. part of the anvil jaw. Alternatively, the left and right hooks can be separate components. Also, the top and bottom left hooks can be integral or separate components. The top and bottom right hooks can likewise be integral or separate components.

In the embodiment of FIG. 6B, the hooks 126b are a separate component attached (either permanently or removably) to instrument 100b to compressively hold the clamp 200b to the instrument 200b. Thus, the hooks 126b sandwich the clamp 200b and instrument 100b together regardless of which side of the instrument 100b the clamp 200b is placed. The clamp in FIG. 6B is shown on the other side of the instrument from clamp 210 of FIG. 6A.

Figure 2:
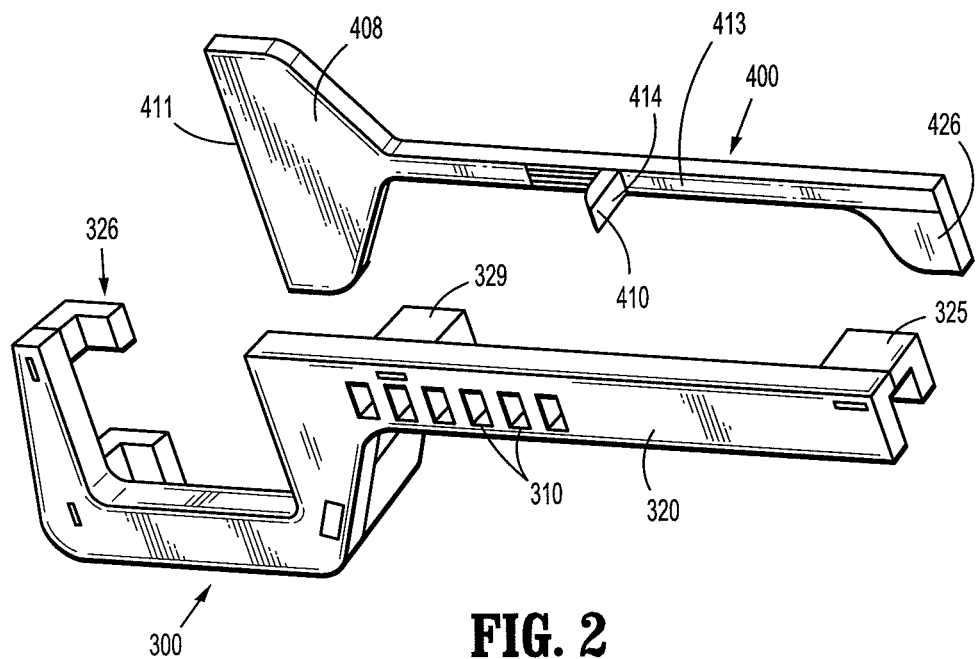
FIG. 2 is an exploded perspective view of an alternate embodiment of a the surgical stapling instrument and clamp of the present disclosure.

In the alternate embodiment of FIG. 2, clamp 400 is similar to clamp 200 and instrument 300 is similar to instrument 100 except for the way the clamp is mounted to the instrument and engages the instrument. Otherwise the clamp and instrument function are the same. Instrument 300 has clamp retaining hooks 326 and proximal and distal hooks 325, 329, similar to hooks 126, 125 and 129 of the embodiment if FIG. 1. Clamp 400 has an enlarged clamp head 408 extending from the elongated portion or member 413 and has a distal tissue engaging surface 411 extending substantially transverse to the longitudinal axis of the elongated body portion for clamping tissue against the anvil jaw of the instrument 300.

Figure 2A:
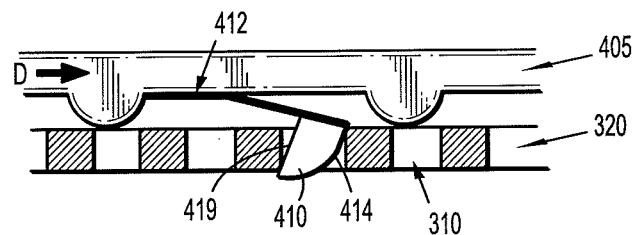
FIG. 2A is an enlarged view of the locking pin of FIG. 2 engaging an opening in the instrument.

Clamp 400 has a locking pin 410 extending radially from its elongated member 413 which is engageable in one of a plurality of openings 310 formed in the elongated portion 320 of the instrument 300. The locking pin 410 extends through one of the openings 320, depending on the axial position of the clamp 400, protruding from the opposing side. In this way, to release the clamp 400, the locking pin 410 is pushed inwardly out of the opening 310 to force the clamp 400 away from the instrument 300 and to disengage the pin 410 from the opening, thereby allowing the clamp 400 to be pulled proximally to a retracted position. Spring 412 on pin 410 biases it into engagement with the respective opening 310. This pin/opening arrangement allows stepped movement for controlled advancement of the clamp 400 as well as locks the clamp in the desired position. That is, operating like a ratchet mechanism, the pin 410 is configured to allow movement of the clamp 400 in the distal direction (see arrow D of FIG. 2A), while preventing retraction. This is due to the curved distal surface 414 allowing the pin 410 to slide out of one opening 310 when sufficient distal force is applied and slide into the next more distal opening 310 while the straight walled or flat surface 419 on the proximal side prevents the pin from sliding proximally out of the opening 310. The clamp 400 can be manually advanced by pushing handle 426 forward.

A locking pin can optionally be positioned on the other side of the clamp 400 (not shown) which is engageble with the openings 310 to enable the clamp 400 to be mounted on the opposing side of the instrument 300. This would necessitate the provision of the hooks on the opposing side of the instrument to mount and retain the clamp 400.

As can be appreciated, the teeth openings 310 are positioned on the elongated portion 320 spaced from the approximation mechanism and the firing mechanism which are slidably received within the elongated portion of the instrument and not shown in the drawings so as not to interfere with these components.

Figure 3:
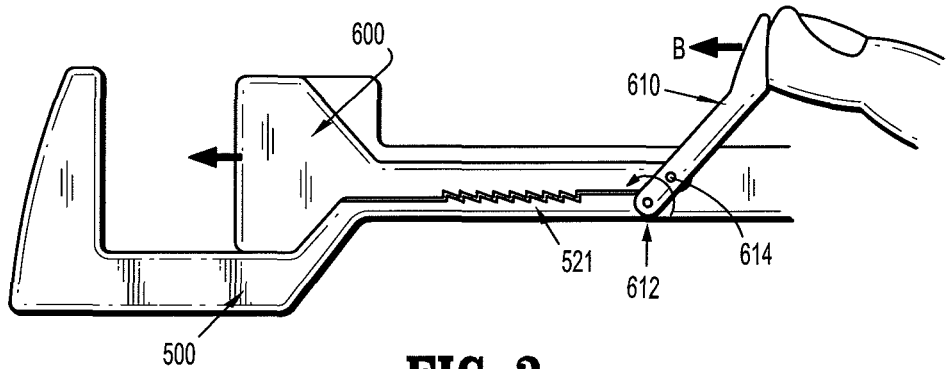
FIG. 3 is a side view of another alternate embodiment of the surgical stapling instrument and clamp of the present disclosure, the clamp shown in the retracted position.
Figure 4:
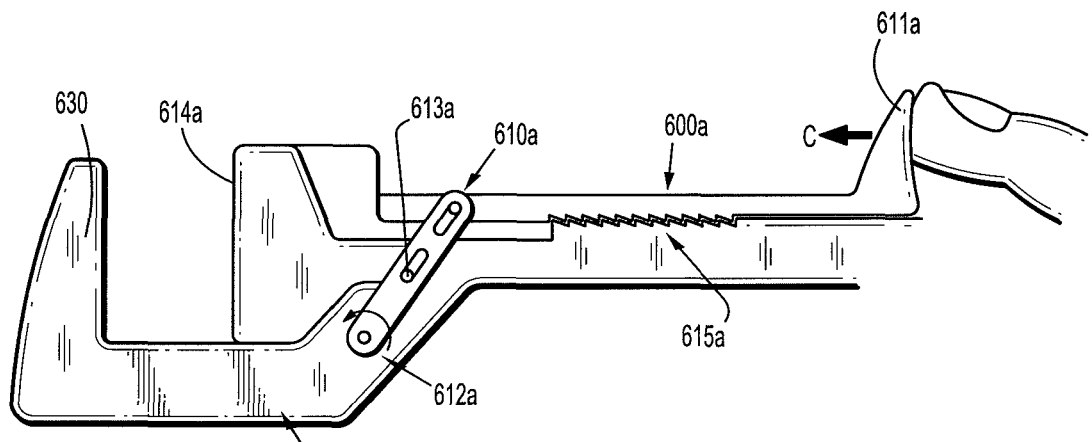
FIG. 4 is a side view of yet another alternate embodiment of the surgical stapling instrument and clamp of the present instrument, the clamp shown in the retracted position.

In the alternate embodiments of FIGS. 3 and 4, a cam is used to approximate the clamp. In FIG. 3, as cam lever 610 is pushed in the direction of arrow B, it rotates the lever about pivot pin 612. Pin 614 connects the lever 610 to the clamp 600 so that counterclockwise rotation of the lever 610 advances the clamp 600. The instrument 500 can include a ratchet mechanism with teeth 521 or alternatively holes such as described above to cooperate with a series of teeth on the clamp similar to teeth 221 or a locking pin similar to pin 410.

In FIG. 4, the cam lever 610a is positioned closer to the cartridge. Pushing on handle 611a in the direction of arrow C, advances the clamp 600a and causes cam lever 610a to rotate counterclockwise about pivot pin 612a. Middle pin 613a is connected to clamp 600a so that pivoting of cam lever 610a advances the clamp 600 distally to enable tissue contacting surface 614a to compress tissue against the anvil jaw 630 of the instrument 500a. Ratchet teeth are shown on the clamp 600a and designated by reference numeral 615a and operate similar to ratchet 220 of FIG. 1. A locking pin similar to locking pin 410 could alternatively be provided.

In use of the foregoing instruments, actuation of the handle mechanism (not shown) causes elongated members to translate distally within the elongated portion, which cause approximation of the jaw members and/or staples to be fired from the cartridge assembly. To return the jaw members to their original position, it is envisioned that the firing handle is at least partially retracted towards its original position, thus causing proximal translation of an elongated member, which causes proximal translation of cartridge assembly with respect to anvil assembly, for example. In some embodiments, a spring can be provided to bias the elongated members, jaw members or handle(s) to the retracted position The cartridge assembly can include two or more rows of staples (which can be staggered) and can also optionally include a knife. The two rows of staples helps reduce the profile of the end effector and may also help provide better detection of margins (the outer limits of the stapled organ). It is also envisioned that one row of staples or more than two rows of staples is used, e.g., two pairs of two rows of staples—one pair on each side of the knife. Also, the number of rows on each side of the knife need not be equal. For example, one row of staples can be provided on one side of the knife and two rows of staples provided on the other side of the knife. The knife can also be provided adjacent the outer row of staples.

In use, the organ or other tissue to be stapled is situated between the cartridge assembly and anvil assembly. Next, guide pin can be manually advanced, or as in some embodiments, the guide pin is advanced automatically upon approximation of the cartridge. Clamp 210 (or the other clamps described herein) is then translated distally in the direction of arrow A in FIG. 1A to compress the tissue against a portion of the end effector (which may temporarily occlude the organ). Next, the jaw members are approximated to clamp tissue therebetween by advancing the cartridge assembly towards the anvil assembly. (It is also contemplated that in alternate embodiments, the anvil assembly can be moved toward the cartridge assembly to clamp tissue or both the cartridge and anvil assembly can be movable toward each other to clamp tissue). Staples are then fired from the cartridge towards the anvil pockets of the anvil assembly where they are deformed by the anvil pockets. The knife, if provided, is translated distally from the cartridge assembly through tissue either during, e.g. along with the firing of the staples, or following the firing of staples. After firing the staples, the guide pin and cartridge assembly are retracted proximally. Retraction can occur either simultaneously or consecutively (sequentially). The clamp 210 is also retracted proximally, such that surgical stapling instrument 100 can be removed from the organ.

The various actuations of surgical stapling instrument 100 to approximate the cartridge and fire the staples can be achieved by myriad techniques. Examples of handles are described in copending provisional patent application Ser. No. 61/050,272, filed May 5, 2008, the entire contents of which are incorporated herein by reference.

Other methods of actuating the surgical stapling instrument 100, including method for performing a lower anterior resection ("LAR"), are also envisioned. For instance, the handle portion may include a single movable handle that may be squeezed multiple times, where each actuation can perform a distinct operation. That is, a first actuation of the movable handle may approximate the jaw members and a second actuation of the same movable handle may deploy staples and knife. Alternatively separate handles, levers, rotation knobs, etc. can be used for approximation and firing.

It is further envisioned that guide pin(s), of the various embodiments, can be independently advanced by a structure disposed on or adjacent the handle portion. Additionally, any combination including a first and second movable handle, knob, slide and button may be used to advance guide pin(s), approximate the jaw members, fire staples, transect tissue, open the jaw members, and proximally translate guide pin(s).

Various embodiments of different knife blades can be utilized such as those described in application Ser. No. 61/050, 272, filed May 5, 2008, which is incorporated herein in its entirety by reference.

It is further envisioned that surgical stapling instrument 100 of the present disclosure does not include a knife. Rather, after the organ has been stapled, the surgeon, if desired, can use another instrument to transect the tissue.

The elongated portion 120 of surgical stapling instrument 100 is shown straight, however, alternatively it could be curved (e.g., gradually curved) and/or bent (e.g., includes a sharp corner or angle) and/or twisted to facilitate access and/or visualization (e.g., into a patient's pelvic cavity). The elongated portion of the clamp 200 would likewise be shaped, e.g. curved or twisted, to conform the instrument for mounting thereon.

In yet additionally envisioned embodiments, cartridge assembly, anvil assembly, knife, and/or staple pusher(s) may be disposable. An example of such a configuration is shown in commonly-owned, U.S. Pat. No. 4,383,634 to Green, the entire contents of which are hereby incorporated by reference herein. Further, surgical stapling instruments of the present disclosure may include a multiple pusher configuration or a single pusher configuration.

The present disclosure also includes a method of using the surgical stapling instruments described above. The method includes the steps of providing a surgical stapling instrument, mounting a clamp on the instrument, using the surgical stapling instrument to clamp tissue, approximate its jaw members, and fire staples (fasteners). The method may also include the steps of advancing a guide pin, transecting tissue, opening the jaw members, releasing the guide pin and releasing the clamp from the tissue.

The present disclosure also relates to another method of using the described surgical instrument. The method, as described above, includes providing a surgical instrument, clamping tissue via the clamp attached to the instrument, approximating the jaw members, firing staples (e.g., simultaneously), and/or cutting tissue (e.g., with a knife disposed in mechanical cooperation with the surgical instrument, or using a separate instrument). In certain embodiments, the instrument is used for lower anterior resection. First, the clamp is actuated, clamping onto intestinal tissue. Then, the interior of the intestinal tissue is washed out or otherwise cleansed. The tissue is then cut and stapled. In this way, the interior intestinal tissue is cleansed up to the location of the clamp, including the area where the jaws will engage the intestinal tissue to be stapled and/or cut, once the jaws are approximated.

The present disclosure also relates to a loading unit configured for releasable engagement with a surgical instrument, the loading unit including a pair of jaw members and configured for releasable engagement with a distal portion of the elongated portion of the surgical instrument. The loading unit can also include a knife. At least one of the jaw members is movable with respect to the other between an open position and an approximated position for engaging body tissue therebetween. The clamp is movable between an open position and an approximated position for engaging body tissue.

The clamp could be packaged with the instrument or could be packaged separately.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed:

1. A surgical fastener applying instrument comprising:
a handle portion;
an elongated portion extending distally from the handle portion and having a longitudinal axis;
a pair of jaw members disposed adjacent a distal portion of the elongated portion, at least one of the jaw members being movable with respect to the other jaw member between an open position and an approximated position for engaging body tissue therebetween, the first jaw member configured to contain a plurality of fasteners arranged in at least one row along its entire length substantially transverse to a longitudinal axis of the elongated portion; and
a removable clamp having an elongated member and a tissue clamping surface extending substantially transverse to a longitudinal axis of the elongated member, the tissue clamping surface extending along a majority of the entire length of the first jaw member, the clamp movable from a proximal position to a distal position for engaging body tissue, the clamp releasably mountable to the elongated portion of the instrument, such that when the removable clamp is released from the elongated portion, the removable clamp is free from contact with any other portion of the surgical fastener applying instrument, the surgical instrument being configured and dimensioned to apply fasteners to tissue both with the removable clamp mounted to the elongated portion and when the removable clamp is released from the elongated portion.

2. The surgical instrument of claim 1, wherein the clamp is independently movable with respect to the jaw members.

3. The surgical instrument of claim 1, wherein a tissue-contacting surface of each of the jaw members is disposed substantially transverse to the longitudinal axis of the elongated portion.

4. The surgical instrument of claim 1, wherein the clamp is mountable to either side of the elongated portion of the instrument.

5. The surgical instrument of claim 4, further comprising a hook configured to secure the clamp on either side of the instrument, the hook protruding transversely from the elongated portion.

6. The surgical instrument of claim 1, further comprising at least one hook extending from the instrument to secure the clamp to the instrument.

7. The surgical instrument of claim 6, wherein the at least one hook is detachable from the instrument and configured to be attached to either side of the instrument for mounting the clamp on either side of the instrument.

8. The surgical stapling instrument of claim 1, wherein the jaw members include a cartridge and anvil assembly, at least the cartridge configured to be removable from the instrument.

9. The surgical stapling instrument of claim 1, wherein the clamp includes an enlarged clamping head extending from the elongated member, the tissue contacting surface formed on the distal end of the clamping head.

10. The surgical instrument of claim 1, wherein a proximal-most portion of the removable clamp is mountable to the elongated portion.

11. The surgical instrument of claim 1, wherein the removable clamp is releasable from the elongated portion in a direction that is transverse to longitudinal axis such that the removable clamp remains parallel to the longitudinal axis.

* * * * *